United States Patent [19]

Sherlock

[11] 4,123,433
[45] Oct. 31, 1978

[54] 2-CYANO-5-(SUBSTITUTED TRIPHENYLMETHYL) PYRIDINES

[75] Inventor: Margaret H. Sherlock, Bloomfield, N.J.

[73] Assignee: Schering Corporation, Kenilworth, N.J.

[21] Appl. No.: 824,026

[22] Filed: Aug. 12, 1977

Related U.S. Application Data

[63] Continuation of Ser. No. 636,010, Nov. 28, 1975, Pat. No. 4,044,140.

[51] Int. Cl.$^2$ ............................................. C07D 213/57
[52] U.S. Cl. ............................... 260/294.9; 260/295 R; 260/295 AM; 424/266
[58] Field of Search ........................ 260/294.9, 295 R

[56] References Cited

U.S. PATENT DOCUMENTS

| | | | |
|---|---|---|---|
| 3,396,224 | 8/1968 | Heyningen | 260/295 R |
| 3,397,273 | 8/1968 | Heyningen et al. | 260/295 R |
| 3,963,732 | 6/1976 | Bruzzese et al. | 260/295 R |

Primary Examiner—Alan L. Rotman
Attorney, Agent, or Firm—Bruce M. Eisen; Raymond A. McDonald; Carver C. Joyner

[57] ABSTRACT

Disclosed herein are novel 5-tritylpicolinic acids, amides, esters and pharmaceutically acceptable salts thereof. Also disclosed are methods for the use of said novel compounds as anti-acne agents.

3 Claims, No Drawings

2-CYANO-5-(SUBSTITUTED TRIPHENYLMETHYL) PYRIDINES

This is a continuation of application Ser. No. 636,010, filed Nov. 28, 1975, now U.S. Pat. No. 4,044,140.

This invention relates to a novel class of compounds useful as anti-acne agents. More particularly, this invention relates to 5-(substituted triphenylmethyl) picolinic acids, esters, amides and pharmaceutically acceptable salts thereof, and to their use in the treatment and alleviation of acne.

The tangible embodiments of this invention are represented by the following structural formula:

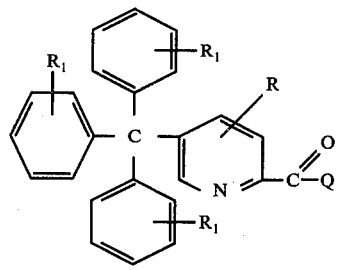

I and the pharmaceutically acceptable salts thereof, wherein R is hydrogen or alkyl; each $R_1$ is a member selected from the group consisting of hydrogen, halogen, hydroxy, alkyl, alkoxy, trifluoromethyl and phenyl; Q is a member selected from the group consisting of hydroxy, cyanoalkoxy, alkoxy, —O-alkylene $NR_2R_3$, glyceryl, $NR_2R_3$, —$NR_2$-alkylene-OH; and $R_2$ and $R_3$ which may be the same or different are members selected from the group consisting of hydrogen and alkyl or $R_2$ and $R_3$ together with the amido nitrogen atom may form a 5 to 7 membered heterocyclic ring which may contain a second heteroatom selected from the group consisting of oxygen and nitrogen.

Although the compounds of this invention may more properly be named as 2-pyridine carboxylic acids, such compounds will be named according to their trivial nomenclature. Thus, for ease in nomenclature and for a more readily recognizable term to one of ordinary skill in the art, the compounds are herein designated as picolinic acids.

As used herein the term "alkyl" means a straight, branched chain or cyclized hydrocarbon having up to 12 carbon atoms. The term "alkoxy" means a straight, branched chain or cyclized hydrocarbon which is bonded to an oxygen atom by a single bond. When such terms are modified by the term "lower" then such radicals contain up to six carbon atoms. Representative of the alkyl and alkoxy groups are methyl, ethyl, n-butyl, t-butyl, octyl, dodecyl, isopropyl, cyclopropyl, cyclopentyl, cycloheptyl, cyclooctyl, methoxy, ethoxy, n-butyloxy, t-butyloxy, octyloxy, dodecyloxy, isopropyloxy, cyclopropyloxy, cyclopentyloxy, cycloheptyloxy, cyclooctyloxy, and the like, with the lower alkyl and lower alkoxy groups being preferred.

The term "—O-alkylene-$NR_2R_3$," which is sometimes also describe herein as "aminoalkyloxy", represents an alkylene group consisting of a divalent straight, branched or cyclized hydrocarbon having up to 12 carbon atoms, which is between an oxygen atom and the $NR_2R_3$ group. Preferably, the alkylene moiety has up to six carbon atoms. Among the preferred "—O-alkylene-$NR_2R_3$" groups are: aminoethoxy, aminopropyloxy, aminovaleryloxy, mono and dialkylaminoethoxy, mono and dialkylaminovaleryloxy, piperidinoethoxy, morpholinoethoxy, piperazinoethoxy, pyrrolidinoethoxy, morpholinopropyloxy, morpholinovaleryloxy and piperazinoisopropyloxy.

Examples of groups represented by "$NR_2R_3$" are amino, mono and dialkylamino, morpholino, pyrrolidino, piperidino and piperazino.

In view of the foregoing definition of the terms "$NR_2R_3$" and "O-alkylene-$NR_2R_3$", the definition of the terms "$NR_2$-alkylene-OH" and "O-alkylene-CN" (cyanoalkoxy) are obvious.

The term "glyceryl" is the radical generally shown as —$OCH_2CHOHCH_2OH$.

Exemplary of the salts of the picolinic acids of Formula I, i.e. wherein "Q" represents hydroxy, are those formed with alkali metals, alkaline earth metals and non-toxic organic bases such as N-methyl glucamine and alcoholamines, preferably diethanolamine.

In those instances wherein the "R" substituent on the picolinic acid moiety is an alkyl group, it is preferably located at the 3-position of the pyridine ring.

The compounds of this invention may be prepared by methods generally known in the art. For example, in the Journal of the American Chemical Society 71, 387–390 (1949) is set forth a convenient procedure for preparing 5-triphenylmethyl-2-chloropyridine. In an analogous manner R-substituted-5-($R_1$-substituted triphenylmethyl)-2-halogeno pyridines may be prepared. Treatment of the latter compounds with cuprous cyanide converts them to the corresponding 2-cyano analog from which the R-substituted-5-($R_1$-substituted triphenylmethyl)-picolinic acid may be prepared by hydrolysis. The foregoing reaction sequence is depicted by the following reaction sequence:

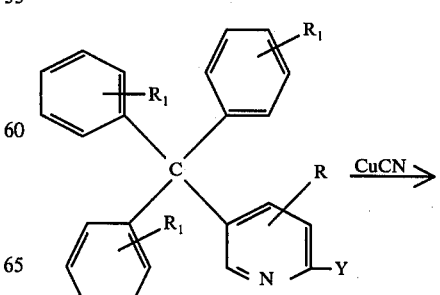

II

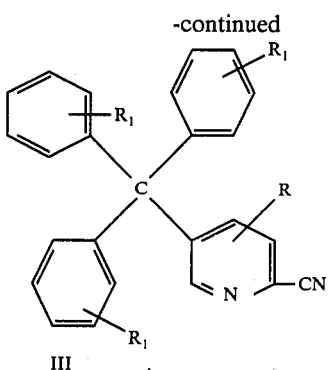

III (1) HOH, KOH,
(2) H⁺

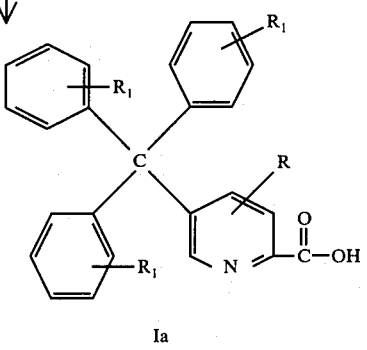

Ia wherein R and $R_1$ are as previously defined and Y represents a halogen.

Standard techniques, such as by heating compound II and cuprous cyanide at elevated temperatures, preferably in the presence of an inert organic solvent, for about 2 to 10 hours, are utilized in the first step of the above reaction. For example, the reaction is very smoothly effected in refluxing dimethylformamide in from about 4 to about 6 hours. Isolation of the 2-cyano analog (III) may be accomplished by standard extraction techniques after the reaction mixture has been quenched; preferably by utilization of a non-water miscible solvent, e.g. benzene, toluene, ethyl ether or the like.

The crude 2-cyano intermediates (III) may directly be converted to the acid via an intermediate alkali metal salt which is then converted to its desired acid form. Standard purification through salt formation and hydrolysis techniques well known to those of ordinary skill in the art may be employed.

To prepare compounds of this invention wherein Q is an activated ester, it is advantageous to utilize the following reaction sequence:

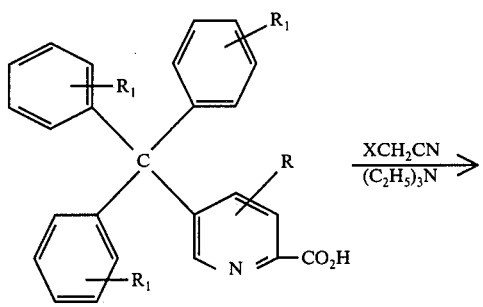

Ia

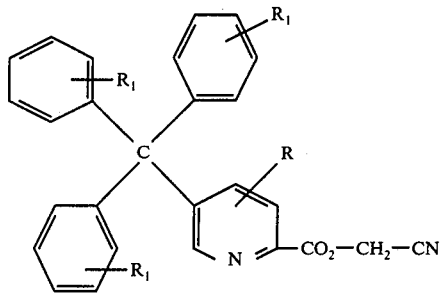

Ib wherein R, $R_1$ and alkylene are as previously defined, and X is a halogen.

Conversion of an R-substituted 5-($R_1$-triphenylmethyl)-picolinic acid (Ia) to the corresponding cyanomethyl ester (Ib) is usually effected by treating the acid at an elevated temperature with a halogenoacetonitrile in the presence of an acid acceptor, such as triethylamine. The reaction is, advantageously, effected in a non-reactive organic solvent such as acetone, methyl ethyl ketone, or the like. The reaction is allowed to proceed for from about 5 to about 20 hours, the reaction mixture is cooled and filtered. The filtrate is concentrated to a residue and triturated with water to yield the desired cyanomethyl ester (Ib). The cyanomethyl ester is a key intermediate from which nearly all of the compounds having the various Q substituents may be prepared. For example, subjecting the cyanomethyl ester to a conventional base catalyzed alcoholysis permits the alcohol to replace the cyanomethyl moiety thereby yielding an alkyl ester derivative. In like manner, by treating the cyanomethyl ester with a dialkylamine at an elevated temperature, the corresponding dialkylamide may be prepared. In fact, from the cyanomethyl intermediate the compounds of this invention wherein Q=alkoxy, —O-alkylene-$NR_2R_3$, —$NR_2R_3$, and —$NR_2$-alkylene-OH may be prepared by the use of the transesterification and amidation techniques. Of course, in those instances wherein the transesterification process designed to produce an amine having a reactive hydrogen, in such reactions the amine groups are first protected (e.g. by standard benzylation procedures) and subsequent to the transesterification, the benzyl or other protective groups are readily cleaved by standard techniques well known in the art. Similarly, when "Q" represents a hydroxyalkylamine, the terminal hydroxy moiety must first be protected e.g. with hydroxy (ether) protecting group and then following transesterification the protecting group removed. These procedures are conducted according to techniques well known in the art.

In those instances wherein it is desired to prepare amides wherein "$NR_2R_3$" is representative of $NH_2$, such R-substituted 5-($R_1$-diphenylmethyl)picolinamides may be prepared by saponification of the corresponding R-substituted 5-($R_1$-diphenylmethyl)-2-cyanopyridine and may be isolated by conventional means.

To prepare compounds of this invention wherein Q is a glyceryl ester, several different routes may be utilized, the choice being determined by the ready availability of the required starting compounds. Preferentially, the ester is prepared by the hydrolysis of an alkylidenedioxypropyl ester of an appropriately substituted triphenylmethyl picolinic acid. The alkylidenedioxypropyl ester is generally prepared by transesterification wherein a reactive alkyl ester (Ib) such as a cyanomethyl ester is transesterified by a cyclic acetal of glycerol (IV). The transesterification is generally effected by heating the reactive ester with the cyclic acetal of glycerol (IV) in the presence of catalytic amounts of tertiary amine catalyst, such as triethylamine at temperatures in the range of 80°-200° C., about 100° C. being preferred. Due to the nature of the transesterification it is advantageous to employ a large excess of cyclic acetal to drive the reaction to completion. Hydrolysis of the alkylidenedioxypropyl ester of the R-substituted 5-($R_1$-triphenylmethyl)-picolinic acid (V) to yield the desired glyceryl ester (Ic) is usually effected by conventional techniques, such as by heating the intermediate in the presence of an acid. For example, by heating the intermediate in dilute acetic acid until the reaction is substantially complete and isolating the glyceryl ester by means known to the art.

The foregoing reaction sequence may be depicted as follows:

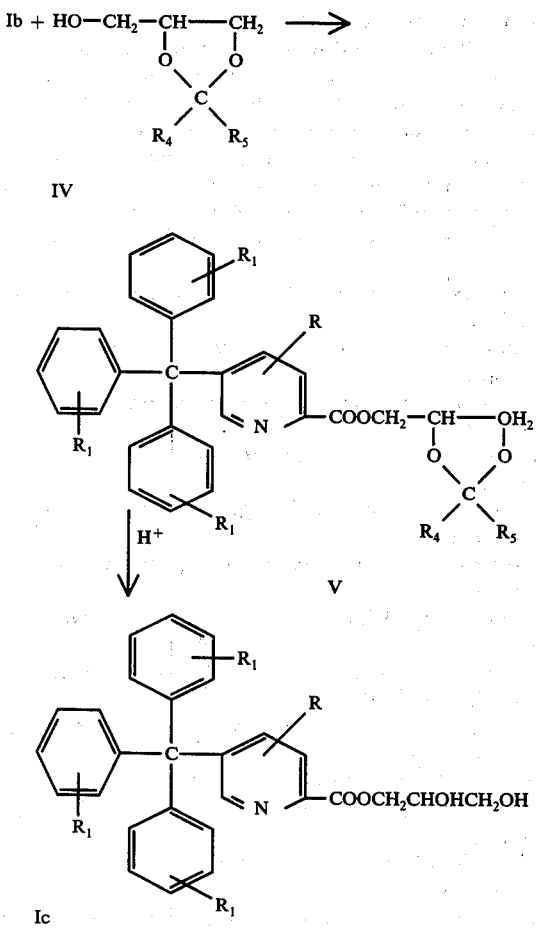

wherein R and $R_1$ are as previously defined, and $R_4$ and $R_5$ are lower alkyl.

The remaining Q substituents may be prepared by standard amidation and esterification procedures well known in the art. The compounds of this invention having a lower alkyl group at the 3-position may be prepared as follows: A 2-amino 3-lower alkyl pyridine (e.g. 2-amino-β-picoline) is reacted with nitrous acid to yield the corresponding 3-lower alkyl pyridone. The latter compound may be converted to the corresponding 3-lower alkyl 5-triphenylmethyl picolinic acid by the procedure set forth hereinabove.

EXAMPLE I

5-(Triphenylmethyl)-Picolinic Acid

A. 2-Bromo-5-(Triphenylmethyl)-Pyridine

Heat at reflux for 3 hours a mixture of 50.6 g. 5-(triphenylmethyl)-2-pyridone and 171 g. phosphorous oxybromide. Pour onto ice and stir on steam bath to decompose excess phosphorous oxybromide. Filter, dry solids, and triturate the product with benzene and ethanol to obtain the product of this example, m.p. 273°-276°.

In a similar manner, subject an equivalent quantity of the following compounds to the process set forth above to obtain thereby the corresponding 2-bromo-pyridine:

5-[(4-biphenyl)diphenylmethyl]-2-pyridone,
5-[(4-chlorophenyl)diphenylmethyl]-2-pyridone,
5-[tris-(4-chlorophenyl)methyl]-2-pyridone,
5-[(4-methylphenyl)diphenylmethyl]-2-pyridone,
5-[bis-(4-fluorophenyl)phenylmethyl]-2-pyridone,
5-[(4-methoxyphenyl)diphenylmethyl]-2-pyridone,
5-[(4-trifluoromethylphenyl)diphenylmethyl]-2-pyridone,
3-methyl-5-[(4-trifluoromethylphenyl)diphenylmethyl]-2-pyridone,
5-[(3-bromophenyl)diphenylmethyl]-2-pyridone,
5-[tris-(3-fluorophenyl)methyl]-2-pyridone,
5-[(3-ethylphenyl)diphenylmethyl]-2-pyridone,
5-[bis-(3-fluorophenyl)phenylmethyl]-2-pyridone,
5-[(3-propoxyphenyl)diphenylmethyl]-2-pyridone,
5-[tris-(3-trifluoromethylphenyl)methyl]-2-pyridone,
3-ethyl-5-[(3-trifluoromethylphenyl)diphenylmethyl]-2-pyridone,
5-[(2-chlorophenyl)diphenylmethyl]-2-pyridone,
5-[(2-isopropylphenyl)diphenylmethyl]-2-pyridone,
5-[bis-(2-fluorophenyl)phenylmethyl]-2-pyridone,
5-[tris-(2-methylphenyl)methyl]-2-pyridone,
5-[(2-ethoxyphenyl)diphenylmethyl]-2-pyridone, and
5-[(2-trifluoromethylphenyl)diphenylmethyl]-2-pyridone.

B. 5-(Triphenylmethyl)-Picolinic Acid

Heat at reflux a mixture of 46.9 g 2-bromo-5-(triphenylmethyl)-pyridine and 21.5 g cuprous cyanide in 450 ml. dimethylformamide for 5½ hr. Pour onto a mixture of ice and 200 ml. ethylene diamine, extract with benzene, dry the benzene extracts, and concentrate. The crude, viscous 2-cyano-5-(triphenylmethyl)-pyridine may be purified by crystallization from acetonitrile to yield a product melting at about 176°-179° or the compound may be converted directly to the acid via the potassium salt by heating it at reflux with 20 g potassium hydroxide pellets in 120 ml. $H_2O$ and 400 ml. ethylene glycol for 15 hr. Filter the hot solution, cool the filtrate which precipitates the potassium salt of the acid. Filter the salt and wash with ethylene glycol, suspend in water, acidify and heat for 1 hr. Filter the acid, dry and recrystallize from acetonitrile, m.p. 215°-217°.

Additional acid is obtained by concentrating the ethylene glycol filtrate of the potassium salt and acidifying.

In addition to the "free" carboxylic acids set forth, the pharmaceutically acceptable salts of the acids are also useful an anti-acne agents. The salts may be prepared in the conventional manner, such as, by reacting the acid with an excess of base in a suitable solvent.

Isolation of the salts is achieved by methods generally used in the art. Exemplary of such bases are the hydroxides, carbonates or bicarbonates of alkali metals, alkaline earth metals and organic bases such as amines (e.g. triethylamine), or, preferably, an alcoholamine such as diethanolamine.

In a similar manner, subject an equivalent quantity of the following compounds to the process set forth above to obtain thereby the corresponding R-substituted-5-($R_1$-substituted)-picolinic acid.

2-bromo-5-[(4-biphenyl)diphenylmethyl]-pyridine,
2-bromo-5-[(4-chlorophenyl)diphenylmethyl]-pyridine,
2-bromo-5-[tris-(4-chlorophenylmethyl)]-pyridine,
2-bromo-5-[(4-methylphenyl)diphenylmethyl]-pyridine,
2-bromo-5-[bis-(4-fluorophenyl)phenylmethyl]-pyridine,
2-bromo-5-[(4-methoxyphenyl)diphenylmethyl]-pyridine,
2-bromo-5-[(4-trifluoromethylphenyl)diphenylmethyl]-pyridine,
2-bromo-3-methyl-5-[(4-trifluoromethylphenyl)diphenylmethyl]-pyridine,
2-bromo-5-[(3-bromophenyl)diphenylmethyl]-pyridine,
2-bromo-5-[tris-(3-fluorophenyl)methyl]-pyridine,
2-bromo-5-[(3-ethylphenyl)diphenylmethyl]-pyridine,
2-bromo-5-[bis(3-fluorophenyl)phenylmethyl]-pyridine,
2-bromo-5-[(3-propoxyphenyl)diphenylmethyl]-pyridine,
2-bromo-5-[tris-(3-trifluoromethylphenyl)methyl]-pyridine,
2-bromo-3-ethyl-5-[(3-methylphenyl)diphenylmethyl]-pyridine,
2-bromo-5-[(2-chlorophenyl)diphenylmethyl]-pyridine,
2-bromo-5-[(2-isopropylphenyl)diphenylmethyl]-pyridine,
2-bromo-5-[bis-(2-fluorophenyl)phenylmethyl]-pyridine,
2-bromo-5-[tris-(2-methylphenyl)methyl]-pyridine,
2-bromo-5-[(2-ethoxyphenyl)diphenylmethyl]-pyridine, and
2-bromo-5-[(2-trifluoromethylphenyl)diphenylmethyl]-pyridine.

EXAMPLE II

Cyanomethyl 5-(Triphenylmethyl)-Picolinate

To a stirred mixture of 5 g. 5-(triphenylmethyl)-picolinic acid and 6.1 g. triethylamine in 150 ml. acetone add 4.5 g. of chloroacetonitrile. Heat the resulting mixture at reflux 15 hr., cool, filter. Concentrate the filtrate to a residue and triturate residue with water, dry. Recrystallize twice from isopropyl ether-ethanol to obtain the product of this example, m.p. 173°–175°.

In a similar manner, subject an equivalent quantity of the following compounds to the process set forth above to obtain thereby the corresponding cyanomethyl R-substituted-5-($R_1$-substituted-triphenylmethyl)-picolinate:

5-[(4-biphenyl)diphenylmethyl]-picolinic acid,
5-[(4-chlorophenyl)diphenylmethyl]-picolinic acid,
5-[tris-(4-chlorophenyl)methyl]-picolinic acid,
5-[(4-methylphenyl)diphenylmethyl]-picolinic acid,
5-[bis-(4-fluorophenyl)phenylmethyl]-picolinic acid,
5-[(4-methoxyphenyl)diphenylmethyl]-picolinic acid,
5[4-(trifluoromethylphenyl)diphenylmethyl]-picolinic acid,
3-methyl-5-[4-(trifluoromethylphenyl)diphenylmethyl]-picolinic acid,
5-[(3-bromophenyl)diphenylmethyl]-picolinic acid,
5-[tris-(3-fluorophenyl)methyl]-picolinic acid,
5-[(3-ethylphenyl)diphenylmethyl]-picolinic acid,
5-[bis-(3-fluorophenyl)phenylmethyl]-picolinic acid,
5-[(3-propoxyphenyl)diphenylmethyl]-picolinic acid,
5-[tris-(3-trifluoromethylphenyl)methyl]-picolinic acid,
3-ethyl-5-[(3-methylphenyl)diphenylmethyl]-picolinic acid,
5-[(2-chlorophenyl)diphenylmethyl]-picolinic acid,
5-[(2-isopropylphenyl)diphenylmethyl]-picolinic acid,
5-[bis(2-fluorophenyl)phenylmethyl]-picolinic acid,
5-[tris-(2-methylphenyl)methyl]-picolinic acid,
5-[(2-ethoxyphenyl)diphenylmethyl]-picolinic acid, and
5-[(2-trifluoromethylphenyl)diphenylmethyl]-picolinic acid.

EXAMPLE III

Methyl 5-(Triphenylmethyl)-Picolinate

Heat at reflux 4 gm. (0.01 mole) of cyanomethyl-5-(triphenylmethyl)picolinate and 2 ml. triethylamine in 50 ml. methanol for 4 hr. Remove methanol under reduced pressure. Triturate solid residue with water and recrystallize from ethylacetate - isopropyl ether, to obtain the product of this example, m.p. 160°–164°.

In a similar manner, subject an equivalent quantity of the following compounds to the process set forth above to obtain thereby the corresponding methyl R-substituted-5-[$R_1$-triphenylmethyl]-picolinate:

cyanomethyl 5-[(4-biphenyl)diphenylmethyl]-picolinate,
cyanomethyl 5-[(4-chlorophenyl)diphenylmethyl]-picolinate,
cyanomethyl 5-[tris-(4-chlorophenyl)methyl]-picolinate,
cyanomethyl 5-[(4-methylphenyl)diphenylmethyl]-picolinate,
cyanomethyl 5-[bis-(4-fluorophenyl)phenylmethyl]-picolinate,
cyanomethyl 5-[(4-methoxyphenyl)diphenylmethyl]-picolinate,
cyanomethyl 5-[4-(trifluoromethylphenyl)diphenylmethyl]-picolinate,
cyanomethyl 3-methyl-5-[4-(trifluoromethylphenyl)diphenylmethyl]-picolinate,
cyanomethyl 5-[(3-bromophenyl)diphenylmethyl]-picolinate,
cyanomethyl 5-[tris-(3-fluorophenyl)methyl]-picolinate,
cyanomethyl 5-[(3-ethylphenyl)diphenylmethyl]-picolinate,
cyanomethyl 5-[bis-(3-fluorophenyl)phenylmethyl]-picolinate,
cyanomethyl 5-[(3-propoxyphenyl)diphenylmethyl]-picolinate,
cyanomethyl 5-[tris-(3-trifluoromethylphenyl)methyl]-picolinate,
cyanomethyl 3-ethyl-5-[(3-methylphenyl)diphenylmethyl]-picolinate,
cyanomethyl 5-[(2-chlorophenyl)diphenylmethyl]-picolinate,
cyanomethyl 5-[(2-isopropylphenyl)diphenylmethyl]-picolinate,
cyanomethyl 5-[bis-(2-fluorophenyl)phenylmethyl]-picolinate, cyanomethyl 5-[tris-(2-methylphenyl)diphenylmethyl]-picolinate,
cyanomethyl 5-[(2-ethoxyphenyl)diphenylmethyl]-picolinate, and
cyanomethyl 5-[(2-trifluoromethylphenyl)diphenylmethyl]-picolinate.

In a similar manner by substituting other alcohols, such as ethanol, propanol, isopropanol, n-butanol or alcohols of the general formula HO-alkylene-NR$_2$R$_3$ for methanol, and by following the process of Example IV the corresponding esters may be prepared.

EXAMPLE IV

N,N-Diethyl-5-(Triphenylmethyl)-Picolinamide

Heat at reflux for 6 hours a mixture of 0.1 mole of cyanomethyl-5-(triphenylmethyl)-picolinate and 0.5 moles of diethylamine. Cool the reaction mixture, pour into water and extract with chloroform. Dry the chloroform layer over anhydrous sodium sulfate and evaporate to obtain thereby the product of this example.

In a similar manner, subject an equivalent quantity of the following compounds to the process set forth above to obtain thereby the corresponding N,N-diethyl-R-substituted-5-(R$_1$-triphenylmethyl)-picolinamide:

cyanomethyl 5-[(4-biphenyl)-diphenylmethyl]-picolinate,
cyanomethyl 5-[(4-chlorophenyl)diphenylmethyl]-picolinate,
cyanomethyl 5-[tris-(4-chlorophenyl)methyl]-picolinate,
cyanomethyl 5-[(4-methylphenyl)diphenylmethyl]-picolinate,
cyanomethyl 5-[bis-(4-fluorophenyl)phenylmethyl]-picolinate,
cyanomethyl 5-[(4-methoxyphenyl)diphenylmethyl]-picolinate,
cyanomethyl 5-[(4-trifluoromethylphenyl)diphenylmethyl]-picolinate,
cyanomethyl 3-methyl-5-[(4-trifluoromethylphenyl)diphenylmethyl]-picolinate,
cyanomethyl 5-[(3-bromophenyl)diphenylmethyl]-picolinate,
cyanomethyl 5-[tris-(3-fluorophenyl)methyl]-picolinate,
cyanomethyl 5-[(3-ethylphenyl)diphenylmethyl]-picolinate,
cyanomethyl 5-[bis-(3-fluorophenyl)-phenylmethyl]-picolinate,
cyanomethyl 5-[(3-propoxyphenyl)diphenylmethyl]-picolinate,
cyanomethyl 5-[tris-(3-trifluoromethylphenyl)methyl]-picolinate,
cyanomethyl 3-ethyl-5-[(3-methylphenyl)diphenylmethyl]-picolinate,
cyanomethyl 5-[(2-chlorophenyl)diphenylmethyl]-picolinate,
cyanomethyl 5-[(2-isopropylphenyl)diphenylmethyl]-picolinate,
cyanomethyl 5-[bis-(2-fluorophenyl)phenylmethyl]-picolinate,
cyanomethyl 5-[tris-(2-methylphenyl)methyl]-picolinate,
cyanomethyl 5-[(2-ethoxyphenyl)diphenylmethyl]-picolinate, and
cyanomethyl 5-[(2-trifluoromethylphenyl)diphenylmethyl]-picolinate.

In a similar manner, by substituting an equivalent quantity of other mono or di-alkylamines or mono or dialcoholamines or heterocyclic amines, such as methylamine, ethylamine, octylamine, dodecylamine, ethanolamine, diethanolamine, piperazine, morpholine, pyrrolidine, piperidine or the like and by following the process set forth in Example IV, the corresponding mono or di-alkylamides may be prepared.

EXAMPLE V

Glyceryl (5-Triphenylmethyl)-Picolinate

A.
β-γ-Isopropylidenedioxypropyl(5-triphenylmethyl)-picolinate

Heat with stirring on a steam bath for 1½ hours a mixture of 4 g of cyanomethyl 5-(triphenylmethyl)-picolinate, 50 ml. of 2,2-dimethyl-1,3-dioxolane-4-methanol and 2 ml. of triethylamine. Treat the reaction mixture with water, cool and filter to yield the product of this step.

B. Glyceryl 5-(Triphenylmethyl)-Picolinate

Heat with stirring on a steam bath for 1 hour a mixture of 4.5 g. of β-γ-isopropylidenedioxypropyl 5-(triphenylmethyl)-picolinate and 90 ml. of 75% acetic acid. Pour the reaction mixture onto ice. Filter and dissolve the resulting solid in ethyl acetate, wash twice with water, dry over MgSO$_4$ and concentrate, recrystallize from acetonitrile m.p. 183°–186° to obtain thereby, the product of this Example.

In a similar manner, subject an equivalent quantity of the compounds enumerated after Example IV to steps A and B of Example V to obtain thereby the corresponding glyceryl R-substituted-5-(R$_1$-substituted-triphenylmethyl)-picolinate.

EXAMPLE VI

5-(Triphenylmethyl)-Picolinamide

Dissolve 5 g. of 5-(triphenylmethyl)-2-cyanopyridine in a mixture consisting of 50 ml. of water and 1.0 liter of methanol. Add 4 g. of potassium hydroxide and heat the mixture at reflux for 15 hours. Remove the methanol under reduced pressure, triturate the residue with water and dry the solids obtained thereby. Crystallize the product from acetonitrile to obtain the product of this example. m.p. 239°–240° C.

In a similar manner, subject an equivalent quantity of the following compounds to the process of Example VI to obtain thereby the corresponding R-substituted-5-(R$_1$-substituted triphenylmethyl)-picolinamide:

5-[(4-biphenyl)-diphenylmethyl]-2-cyanopyridine,
5-[(4-chlorophenyl)diphenylmethyl]-2-cyanopyridine,
5-[tris-(4-chlorophenyl)methyl]-2-cyanopyridine,
5-[(4-methylphenyl)diphenylmethyl]-2-cyanopyridine,
5-[bis-(4-fluorophenyl)phenylmethyl]-2-cyanopyridine,
5-[(4-methoxyphenyl)diphenylmethyl]-2-cyanopyridine,
5-[(4-trifluoromethylphenyl)diphenylmethyl]-2-cyanopyridine,
3-methyl-5-[(4-trifluoromethylphenyl)diphenylmethyl]-2-cyanopyridine,
5-[(3-bromophenyl)diphenylmethyl]-2-cyanopyridine,
5-[tris-(3-fluorophenyl)methyl]-2-cyanopyridine,
5-[(3-ethylphenyl)diphenylmethyl]-2-cyanopyridine, 5-]bis-(3-fluorophenyl)phenylmethyl]-2-cyanopyridine,
5-[(3-propoxyphenyl)diphenylmethyl]-2-cyanopyridine,
5-[tris-(3-trifluoromethylphenyl)methyl]-2-cyanopyridine,
3-ethyl-5-[(3-methylphenyl)diphenylmethyl]-2-cyanopyridine,
5-[(2-chlorophenyl)diphenylmethyl]-2-cyanopyridine,
5-[(2-isopropylphenyl)diphenylmethyl]-2-cyanopyridine,
5-[bis-(2-fluorophenyl)phenylmethyl]-2-cyanopyridine,
5-[tris-(2-methylphenyl)methyl]-2-cyanopyridine,
5-[(2-ethoxyphenyl)diphenylmethyl]-2-cyanopyridine, and
5-[(2-trifluoromethylphenyl)diphenylmethyl]-2-cyanopyridine.

The following is a "general" method for preparing "pharmaceutically acceptable salts" of the 5-(substituted triphenylmethyl)-picolinic acids:

EXAMPLE VII

5-(Triphenylmethyl)-Picolinic Acid Diethanolamine Salt

Combine 5.5 g. of 5-(triphenylmethyl)-picolinic acid and 1.6 g. of diethanolamine in 200 ml. of ethanol and heat to form a solution, then cool to precipitate the salt. Recrystallize from ethanol to give the title compound, m.p. 206°–209°.

Acne is a common inflammatory disease in areas of the skin wherein sebaceous glands are largest, most numerous, and most active. It is characterized by the appearance of comedones, pustles, papules, inflamed nodules, and in extreme cases infected sacs. In acne *Corynebacterium acnes* and *Staphylococcus albus*, common residents of the skin and sebaceous glands (especially of the adolescent), are known to aggravate the existing inflammatory condition by releasing enzymes (lipase) which break down the lipid in the sebum with the concomitant release of irritating free fatty acids (FFA). Thus, an effective anti-acne agent ought be one which can prevent or substantially reduce the breakdown of lipid in the sebum thereby exerting an anti-inflammatory effect upon the skin. Ideally, the anti-ance agent should be effective topically in order to minimize the advent of untoward side effects which may occur during systemic treatment. For instance, frequently used anti-acne agents (e.g. the tetracyclines) are related to side effects which appear with the long term systemic treatment usually required in treating acne. These adverse effects include gastrointestinal irritation, photosensitivity reactions, dizziness, nausea and vomiting. Thus, there is need for effective topically applied antiacne agents. The compounds of this invention fill such a need.

When tested in vitro by a slightly modified version of the test procedure described by A. Shalita and V. Wheatley, in J. Invest. Dermatol. 54, 413 (1970), the compounds of this invention were shown to substantially inhibit the formation of free fatty acids from triglycerides by bacterial lipases, including those formed by *Corynebacterium acnes*. The free fatty acids produced were assayed by the automated colorimetric method of C. Dalton and C. Kowalski as described in Clinical Chem. 13, 744 (1967). Further, the test results clearly demonstrate that the anti-lipase activity of the compounds of this invention is substantially greater than that of hexachlorophene, or that of tetracycline.

Additionally, neither hexachlorophene nor tetracycline exhibit substantial in vivo topical activity in test animals whereas the compound of this invention do. Moreover, the instant compounds are substantially devoid of overt skin irritation upon repeated topical administration. They also exhibit little systemic toxicity following repeated topical application or upon systemic dosing via oral or intraperitoneal administration.

As mentioned, the compounds of this invention are effective antibacterial agents, particularly against *Corynebacterium acnes* and *S. albus*. Additionally, the compounds of this invention are effective against other gram-positive organisms and they also are antitrichomonal; they being particularly effective against *T. vaginalis*. As such, the compounds may be used in the conventional manner for treating gram-positive infections and for treating trichomonal infections. Potency assays and formulations for such uses utilize standard techniques.

The compounds of this invention are administered topically in pharmaceutical compositions having the conventional excipients. The compositions may be in the form of lotions, creams, aerosols and ointments. In these compositions, the active compound is present in the range of from about 0.5% to about 10% by weight, administration being from about 2 to about 5 times daily.

As is usually the case wherein a family of compounds exhibit a particular utility, certain members for one reason or another are preferred over others. In the instant case, a preferred group of compounds are those embraced by formula I wherein R and $R_1$ are hydrogen and Q is as defined for formula I.

Another preferred group of compounds within the genus defined by formula I are those wherein R and $R_1$ are as defined in said claim and Q in combination with the carbonyl to which it is attached forms a glyceryl ester.

An especially preferred compound within the genus defined by formula I is the one wherein R and $R_1$ are hydrogen and Q is hydroxy including the pharmaceutically acceptable salts thereof.

The following Examples (i.e. Examples VIII through XII inclusive) are directed to topical formulations in which the compounds of this invention may be utilized to elicit an antiacne response. The formulations are prepared by methods known in the art using the active compound in the form of a "micronized" solid.

EXAMPLE VIII

| Ointment | mg/gm |
|---|---|
| 5-tritylpicolinic Acid diethanolamine salt | 20.0 |
| Propylene Glycol USP | 40.0 |
| Mineral Oil, USP | 50.0 |
| White Petrolatum, USP to make | 1.0 g. |

EXAMPLE IX

| Ointment | mg/gm |
|---|---|
| Glyceryl (5-Triphenylmethyl)-picolinate | 20.0 |
| Propylene Glycol, USP | 40.0 |
| Stearyl Alcohol, USP | 50.0 |
| Polyethylene Glycol 400, USP | 600.0 |
| Polyethylene Glycol 4000, USP to make | 1.0 g. |

EXAMPLE X

| Gel | mg/gm |
|---|---|
| 5-tritylpicolinic Acid | 20.0 |
| Propylene Glycol, USP | 300.0 |
| Polyethylene Glycol, 400 USP | 660.0 |
| Butylated Hydroxytoluene | 5.0 |
| Carbopol 940P | 15.0 |
| Titanium Dioxide, USP | 10.0 |
| Sodium Hydroxide, USP | 0.7 |

EXAMPLE XI

| Cream | mg/gm |
|---|---|
| 5-tritylpicolinic Acid | 20.0 |
| Stearic Acid, USP | 60.0 |
| Glyceryl Monostearate, Cosmetic | 100.0 |
| Propylene Glycol, USP | 50.0 |
| Polyoxyethylene Sorbitan Monopalmitate, Cosmetic | 50.0 |
| Sorbitol Solution, USP | 30.0 |
| Benzyl Alcohol, N.F. | 10.0 |
| Purified Water, USP to make | 1.0 gm. |

EXAMPLE XII

| Glycol Ointment | mg/gm |
|---|---|
| 5-tritylpicolinic Acid diethanolamine salt | 20.0 |
| Propyl Glycol Monostearate | 20.0 |
| Propylene Glycol, USP | 100.0 |

| -continued | |
|---|---|
| Glycol Ointment | mg/gm |
| White Wax USP | 60.0 |
| White Petrolatum qs to make | 1.0 gm. |

I claim:
1. A compound of the formula

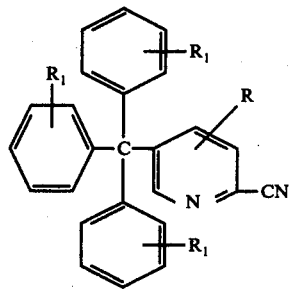

and the pharmaceutically acceptable salts thereof wherein R is hydrogen or alkyl; each $R_1$ is a member selected from the group consisting of hydrogen, hydroxy, alkyl, alkoxy, trifluoromethyl and phenyl wherein said alkyl or alkoxy contains up to 12 carbon atoms.

2. A compound of claim 1 wherein R is hydrogen and each $R_1$ is as defined in said claim.

3. The compound of claim 2 wherein R and each $R_1$ are hydrogen said compound being 2-cyano-5-(triphenylmethyl)-pyridine.